US00RE43795E

(19) United States
(12) Reissued Patent
Yonehara et al.

(10) Patent Number: US RE43,795 E
(45) Date of Reissued Patent: Nov. 6, 2012

(54) METHOD OF PRE-TREATING SAMPLE FOR MEASURING SACCHARIFIED AMINE AND METHOD OF MEASURING SACCHARIFIED AMINE

(75) Inventors: Satoshi Yonehara, Osaka prefecture (JP); Tsuguki Komori, Gifu prefecture (JP)

(73) Assignee: ARKRAY, Inc., Kyoto (JP)

(21) Appl. No.: 12/903,760

(22) Filed: Oct. 13, 2010

Related U.S. Patent Documents

Reissue of:

(64) Patent No.: 7,449,305
Issued: Nov. 11, 2008
Appl. No.: 10/492,140
PCT Filed: Oct. 9, 2002
PCT No.: PCT/JP02/10463
§ 371 (c)(1),
(2), (4) Date: Apr. 6, 2004
PCT Pub. No.: WO03/033729
PCT Pub. Date: Apr. 24, 2003

(30) Foreign Application Priority Data

Oct. 11, 2001 (JP) ..... 2001-314218

(51) Int. Cl.

| | |
|---|---|
| ***C12Q 1/26*** | (2006.01) |
| ***C12Q 1/37*** | (2006.01) |
| ***C12N 9/06*** | (2006.01) |
| ***C12N 9/52*** | (2006.01) |
| ***G01N 33/92*** | (2006.01) |
| ***G01N 33/00*** | (2006.01) |

(52) U.S. Cl. ..... 436/87; 436/63; 436/66; 436/67; 436/71; 436/86; 435/23; 435/25; 435/191; 435/220

(58) Field of Classification Search ..... 436/63, 436/66, 67, 71, 86, 87; 435/23, 25, 28, 191, 435/220

See application file for complete search history.

(56) References Cited

U.S. PATENT DOCUMENTS 5,712,138 A 1/1998 Kato et al. ..... 135/189

(Continued)

FOREIGN PATENT DOCUMENTS

CN 1340099 3/2002

(Continued)

OTHER PUBLICATIONS

N. Yoshida et al., "Primary structures of fungal fructosyl amino acid oxidases and their application to the measurement of glycated proteins" European Journal of Biochemistry, 242(3): 499-505 (Dec. 15, 1996); XP002089646.

(Continued)

*Primary Examiner* — Maureen Wallenhorst

(74) *Attorney, Agent, or Firm* — Morgan, Lewis & Bockius LLP

(57) ABSTRACT

The present invention provides a method of pretreating a sample containing a glycated amine as an analyte, thereby enabling highly reliable measurement of a glycated amine. A glycated amino acid in the sample is degraded by causing a fructosyl amino acid oxidase (FAOD) to act thereon, and thereafter, a FAOD further is caused to act on the glycated amine as the analyte in the sample to cause a redox reaction. The amount of the glycated amine is determined by measuring the redox reaction. The substrate specificity of the FAOD caused to act on the glycated amino acid may be either the same as or different from that of the FAOD caused to act on the glycated amine. When using the same FAOD, a FAOD is caused to act on the glycated amino acid to degrade it, and thereafter, the sample is treated with a protease to inactivate the FAOD and also to degrade the glycated amine. Then, the same FAOD further is added so that the FAOD acts on the degradation product obtained to cause a redox reaction, and the redox reaction is measured.

39 Claims, 1 Drawing Sheet

U.S. PATENT DOCUMENTS

| | | | | |
|---|---|---|---|---|
| 5,789,221 | A | 8/1998 | Kato et al. | 435/190 |
| 5,824,527 | A | 10/1998 | Kato et al. | 435/191 |
| 5,985,591 | A * | 11/1999 | Yonehara et al. | 435/28 |
| 6,008,006 | A | 12/1999 | Torrens et al. | 435/23 |
| 6,033,867 | A | 3/2000 | Kato et al. | 435/25 |
| 6,797,503 | B1 | 9/2004 | Ishimaru et al. | 435/23 |
| 7,070,948 | B1 | 7/2006 | Sakaue et al. | 435/23 |
| 7,250,269 | B2 | 7/2007 | Kouzuma et al. | 435/25 |
| 7,449,305 | B2 * | 11/2008 | Yonehara et al. | 435/25 |
| 2005/0101771 | A1 | 5/2005 | Kouzuma et al. | 435/25 |

FOREIGN PATENT DOCUMENTS

| | | |
|---|---|---|
| EP | 0737744 | 10/1996 |
| EP | 0864647 | 9/1998 |
| EP | 0921198 | 6/1999 |
| JP | 7-289253 | 7/1995 |
| JP | 7-289253 | 11/1995 |
| JP | 8-154672 | 6/1996 |
| JP | 8-154672 | 8/1996 |
| JP | 8-298996 | 11/1996 |
| JP | 8-336386 | 12/1996 |
| JP | 10-14596 | 1/1998 |
| JP | 10-99098 | 4/1998 |
| JP | 11-243950 | 9/1999 |
| JP | 2000-166596 | 6/2000 |
| JP | 2000-180439 | 6/2000 |
| JP | 2001-54398 | 2/2001 |
| JP | 2001-95598 | 4/2001 |
| JP | 2001-215229 | 8/2001 |
| WO | 97/13872 | 4/1997 |
| WO | WO 97/13872 | 4/1997 |
| WO | 97/20039 | 6/1997 |
| WO | WO 97/20039 | 6/1997 |
| WO | 02/061119 | 8/2002 |
| WO | WO 02/061119 | 8/2002 |

OTHER PUBLICATIONS

Y. Sakai et al., Production of fungal fructosyl amino acid oxidase useful for diabetic diagnosis in the peroxisome of Candida boidinii FEBS Letters, Elsevier, Amsterdam, NL, 459(2): 233-237 (Oct. 8, 1999); XP004260353.

European Search Report for EP 10005386, dated Aug. 25, 2010.

Yoshida et al., "Distribution and Properties of Fructosyl Amino Acid Oxidase in Fungi", Applied and Environmental Microbiology, Dec. 1995, vol. 61, No. 12, p. 4487-4489.

Progress in Food and Nutrition Science, (1981), vol. 5, No. 5, No. 1-6, p. 265-278.

Fujiwara et al., "Conversion of Substrate Specificity of Glycated Amino Acid Oxidase Derived from Fusarium oxysporum", Abstracts of Annual Meeting 2000, The Society for Biotechnology, p. 184 (with partial abstract).

Maki Fujiwara, et al., "Conversion of Substrate Specificity of Glycated Amino Acid Oxidase Derived from Fusarium oxysporum", Abstracts of Annual Meeting 2000, The Society for Biotechnology, p. 184 (with partial abstract).

Progress in Food and Nutrition Science, (1981), vol. 5, No. 1-6, p. 265-278.*

* cited by examiner

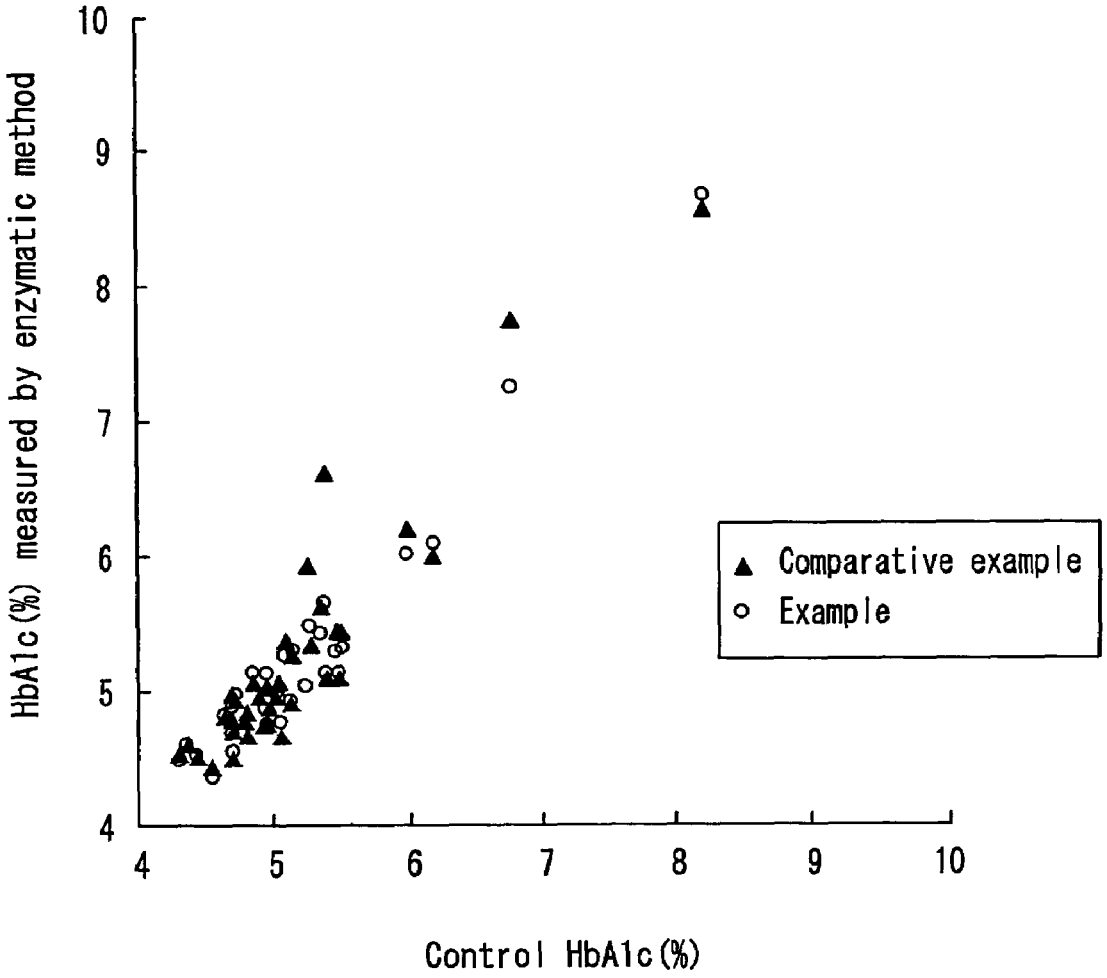
10
9
8
7
6
5
4
HbA1c(%) measured by enzymatic method
4
5
6
7
8
9
10
Control HbA1c(%)
Comparative example
Example

METHOD OF PRE-TREATING SAMPLE FOR MEASURING SACCHARIFIED AMINE AND METHOD OF MEASURING SACCHARIFIED AMINE

Matter enclosed in heavy brackets [ ] appears in the original patent but forms no part of this reissue specification; matter printed in italics indicates the additions made by reissue.

TECHNICAL FIELD

The present invention relates to a method of pretreating a sample for measurement of a glycated amine and to a method of measuring a glycated amine.

BACKGROUND ART

Conventionally, the measurement of the amount of an analyte in a sample using a redox reaction has been utilized for a wide range of applications. For example, such measurement has been utilized for measuring glycated amines (glycated proteins, glycated peptides, glycated amino acids, etc.) in applications such as biochemical analyses, clinical tests, and the like.

In particular, glycated proteins in blood, especially glycated hemoglobins in erythrocytes, serve as important indexes in the diagnosis, treatment, etc. of diabetes, because they reflect the patient's past history of blood glucose levels. Such glycated proteins in erythrocytes are measured using a redox reaction, for example, in the following manner.

First, erythrocytes are hemolyzed to prepare a sample. Then, a fructosyl amino acid oxidase (hereinafter referred to as "FAOD") is added to this hemolyzed sample. The FAOD acts on a glycation site of a glycated protein to cause a redox reaction, thereby forming hydrogen peroxide. The amount of the hydrogen peroxide corresponds to the amount of the glycated protein. Subsequently, a peroxidase (hereinafter referred to as "POD") and a reducing agent that develops color by oxidation are added to the sample so that a redox reaction occurs between the hydrogen peroxide and the reducing agent with the POD as a catalyst. This redox reaction causes the reducing agent to develop color, and the amount of the hydrogen peroxide can be determined by measuring the color developed. As a result, the amount of the glycated protein in the erythrocytes can be determined.

DISCLOSURE OF INVENTION

However, methods of measuring a glycated protein using such a redox reaction have a problem in that, for example, more hydrogen peroxide may be formed than is corresponding to the glycated protein actually contained in a sample. Besides, depending on the patient, the measured value of a glycated protein may leap up temporarily, so that a reliable measurement cannot be performed. Therefore, further improvement in the accuracy of the measurement is desired in the above-described methods. Moreover, not only in the methods using a redox reaction but also in methods of measuring glycated amine using, for example, an antigen-antibody reaction, improvement in the accuracy of measurement is desired.

Therefore, it is an object of the present invention to provide a method of pretreating a sample for measurement of a glycated amine, thereby enabling highly reliable measurement of the glycated amine.

In order to achieve the above object, the present invention provides a method of pretreating a sample containing a glycated amine as an analyte, including: causing a FAOD to act on a glycated amino acid or a glycated peptide present in the sample other than the glycated amine as the analyte so as to remove the glycated amino acid or the glycated peptide by degrading it.

It is to be noted that "FAOD" merely is a generic name and the substrate thereof is not limited to glycated amino acids. For example, FAODs act also on glycated peptides. Furthermore, in the present invention, a "glycated peptide" refers to the one with the length that allows FAODs to act thereon. For example, it refers to the one having 2 to 6 amino acid residues. Accordingly, the term "glycated proteins" as used in the present invention includes glycated proteins and also glycated peptides with the length that does not allow FAODs to act thereon. Examples of the glycated amine as the analyte include glycated proteins, glycated peptides, and glycated amino acids.

The inventors of the present invention have conducted in-depth researches to improve the accuracy of the measurement and finally found out the following fact. In whole blood, not only a glycated amine as an analyte but also a free-state glycated amino acid and a free-state glycated peptide other than the analyte are present inherently. FAODs also act on such a glycated amino acid and a glycated peptide. Thus, when a glycated amine is measured using a FAOD as described above, a redox reaction occurs not only between the glycated amine as the analyte and the FAOD, but also between the glycated amino acid or glycated peptide other than the analyte and the FAOD, so that the measured value of the analyte increases seemingly. Moreover, regarding the above-described problem that some patients show considerable variation in the measured value depending on the time when the blood is collected even though the measurement is carried out by the above-described method with respect to the whole blood samples collected from the same patient under the same conditions, the inventors of the present invention also found out the following fact. This problem is seen mainly in patients after being put on an intravenous drip or the like. For example, if a saccharide such as glucose and any of various amino acids are administered via an intravenous drip or the like, a glycated amino acid is formed from such exogenous substances. As a result, the glycated amino acid increases temporarily, which causes the above-described variation in measured value. Such a phenomenon is observed not only in the methods using a redox reaction but also in the methods using an antigen-antibody reaction, for example. Thus, based on these findings, the inventors of the present invention discovered that, even if a whole blood sample contains a glycation product other than the analyte, such as a glycated amino acid or glycated peptide present homeostatically or an exogenous glycated amino acid present temporarily, the seeming increase in the measured value can be suppressed by pretreating the sample in advance so as to cause a degradation FAOD to act on the glycated amino acid or glycated peptide other than the analyte to degrade it as in the present invention. This allows the accuracy of the measurement to be improved. In addition, since this allows blood to be collected any time regardless of whether or not the patients were put on an intravenous drip, for example, the labor of patients can be reduced. Therefore, by applying the method of pretreating a sample according to the present invention to, for example, the measurement of a glycated hemoglobin using the above described methods, the reliability of the glycated hemoglobin as an index in the diagnosis and the like of diabetes increases. As a result, the methods become useful in the field of clinical medicine and the like.

Next, the present invention provides a method of measuring an amount of a glycated amine as an analyte in a sample, including: pretreating the sample by the above-described pretreatment method of the present invention so as to remove the glycated amino acid or the glycated peptide present in the sample other than the glycated amine as the analyte by degrading it; then causing a FAOD to act on the glycated amine to cause a redox reaction; and measuring the redox reaction to determine the amount of the glycated amine.

For the reason described above, the accuracy of the measurement can be improved by such a method for measurement. Hereinafter, a FAOD used for degrading the glycated amino acid or the glycated peptide other than the analyte is referred to as a "degradation FAOD" and a FAOD caused to act on the glycated amine to measure it is referred to as a "measurement FAOD" in the present invention. Furthermore, the glycated amino acid or glycated peptide present in the sample other than the glycated amine as the analyte hereinafter also is referred to as the "non-analyte glycation product".

Examples of the method for measurement according to the present invention include a first method in which FAODs having substrate specificities different from each other are caused to act on a non-analyte glycation product and a glycated amine as an analyte, respectively, and a second method in which the same FAOD is caused to act on them.

As described later, there are various FAODs, e.g., a FAOD that acts on a glycated α-amino group, a FAOD that acts on a glycated amino group in a side chain (hereinafter also referred to as a "glycated side-chain amino group) of an amino acid residue such as a lysine residue or an arginine residue, and a FAOD that acts on both a glycated α-amino group and a glycated side-chain amino group, and their substrate specificities vary depending on the type of FAODs. In the measurement of a glycated amine, the amount of the glycated amine can be measured by causing a FAOD to act on any of the glycated α-amino group, the glycated side-chain amino group, and both the glycated α-amino group and the glycated side-chain amino group.

In the first method of the present invention, it is preferable that the degradation FAOD caused to act on the non-analyte glycation product has a substrate specificity different from that of the measurement FAOD caused to act on the glycated amine as the analyte. With this configuration, the glycation site of the non-analyte glycation product is degraded with the degradation FAOD, and then, with regard to the glycated amine, the glycation site thereof not subjected to the action of the degradation FAOD is subjected to the action of the measurement FAOD having a substrate specificity different from that of the degradation FAOD. Thus, the influence of the non-analyte glycation product can be eliminated so that the accuracy of the measurement is improved.

Specifically, when the non-analyte glycation product has a glycated α-amino group and the glycated amine as the analyte has a glycated α-amino group and a glycated side-chain amino group, for example, it is preferable that the degradation FAOD is specific for a glycated α-amino group, and the measurement FAOD is specific for a glycated α-amino group and a glycated side chain of an amino acid residue. Since the measurement FAOD acts on both a glycated α-amino group and a glycated side-chain amino group, it also acts on the non-analyte glycation product having a glycated α-amino group when used in conventional methods, as described above. However, in the present invention, since the glycation site of the non-analyte glycation product is degraded with the degradation FAOD specific for a glycated α-amino group in advance, there is no chance that the measurement FAOD may act thereon. As a result, the seeming increase in the measured value is suppressed so that the accuracy of the measurement is improved. Moreover, it is possible to cause the measurement FAOD to act only on the glycated side-chain amino group of the glycated amine since the measurement FAOD acts on both a glycated α-amino group and a glycated side-chain amino group as described above and the glycated α-amino group of the glycated amine also is degraded with the degradation FAOD. Therefore, this method particularly is useful for measurement of a glycated amine that is characterized by the amount of the glycated side-chain amino group. Examples of such a glycated amine include glycated lysine having a glycated ϵ-amino group and glycated albumin.

When using different FAODs as described above, it is preferable that the glycated amine is degraded with a protease to give a degradation product of the glycated amine either before or after causing the degradation FAOD to act on the non-analyte glycation product and the above-described redox reaction is caused by causing the measurement FAOD to act on the degradation product. The degradation of the glycated amine is carried out because, when the analyte is a glycated protein, FAODs have properties that they do not act on glycated proteins easily whereas they act on the glycated peptides as described above and glycated amino acids more easily, and act on glycated amino acids still more easily than on the glycated peptides. Moreover, the reason why the protease treatment may be carried out either before or after the degradation treatment of the non-analyte glycation product is that, since the measurement FAOD can act also on the glycation site other than that on which the degradation FAOD acts as described above, the degradation FAOD treatment does not have any influence on the measurement of the glycated amine itself. Also, when the analyte is a glycated peptide, it is preferable to carry out a protease treatment because the FAOD can act still more easily if the glycated peptide is degraded with a protease to still shorter glycated peptides or glycated amino acids.

In the present invention, unless otherwise stated, "a glycated amino acid and glycated peptide as non-analyte glycation products" refer to those contained in a sample before the degradation by the protease treatment and do not include a degradation product of a glycated protein or a glycated peptide as an analyte obtained by the protease treatment.

Next, as the second method of the present invention, it is preferable that the degradation FAOD is caused to act on the non-analyte glycation product, thereafter, the glycated amine is degraded with a protease to give a degradation product of the glycated amine, and the above-described redox reaction is caused by adding the same FAOD as the degradation FAOD so that it acts on the degradation product. The second method is useful, for example, when the non-analyte glycation product is a glycated amino acid and the glycated amine as the analyte is a glycated protein or a glycated peptide.

Specifically, it is preferable that the degradation FAOD is inactivated with the protease. As described above, FAODs have properties that they do not act on glycated proteins easily and act on glycated amino acids still more easily than on glycated peptides. Thus, when the non-analyte glycation product is, for example, a glycated amino acid, it can be said based on chemical kinetics of enzymes that, even though a degradation FAOD is added, it does not act on a glycated protein and hardly acts on a glycated peptide within a treatment period for degrading the glycated amino acid. However, if the activity of the degradation FAOD still remains during the protease treatment performed subsequently, the remaining degradation FAOD acts on a glycated protein degradation product (such as glycated peptides and glycated amino acids)

or a glycated peptide degradation product (such as shorter glycated peptides and glycated amino acids) obtained while the glycated amine as the analyte is being degraded with the protease. Therefore, when the measurement FAOD is added after the protease treatment, part of the glycated protein degradation product or the like already is subjected to the action of the degradation FAOD. As a result, contrary to what is intended, the accuracy of the measurement may be deteriorated. However, if the protease treatment performed to degrade a glycated protein or the like serves to inactivate the remaining degradation FAOD at the same time as described above, the glycated protein degradation product or the like obtained by the protease treatment remains unreacted with the degradation FAOD and thus can react with the measurement FAOD added subsequently. As a result, the accuracy of the measurement can be improved.

The second method also is useful when the analyte is a glycated protein and the non-analyte glycation product is a glycated peptide, for example. This is because, when the degradation FAOD is caused to act on the glycated peptide, it does not act on the glycated protein within a treatment period for degrading the glycated peptide.

On the other hand, even if the degradation FAOD is not inactivated by the protease treatment as described above, highly accurate measurement also can be realized by, for example, adjusting the amounts of the degradation FAOD and the measurement FAOD to be added to the sample. In this case, the ratio (activity ratio A:B) of the degradation FAOD (A) to the measurement FAOD (B) preferably is set in a range from 1:10 to 1:50,000. When the ratio of the degradation FAOD to the measurement FAOD is in the above-described range, if the degradation FAOD remains during the protease treatment, the remaining degradation FAOD does not act on the glycated peptide as the analyte, not to mention on a glycated protein, as easily as on the glycated amino acid as the non-analyte glycation product, as understood from the chemical kinetics of enzymes. This also applies to the case where the non-analyte glycation product is a glycated peptide and the glycated amine as the analyte is a glycated protein.

In the method of the present invention, as the protease, although not particularly limited, at least one protease selected from the group consisting of metalloproteinases, bromelain, papain, trypsin, proteinase K, subtilisin, and aminopeptidase can be used, for example.

When the analyte is a glycated hemoglobin as described later, the protease is the one that degrades the glycated hemoglobin selectively, and at least one protease selected from the group consisting of metalloproteinases, bromelain, papain, trypsin derived from porcine pancreas, and protease derived from Bacillus subtilis preferably is used. Among these, metalloproteinases and protease derived from Bacillus subtilis are more preferable, and metalloproteinases are particularly preferable. By using such a protease, only the glycated hemoglobin can be measured because glycated proteins other than the glycated hemoglobin hardly are degraded with the protease and thus a FAOD hardly acts on the glycated proteins other than the glycated hemoglobin.

In the present invention, the sample used for measurement is not particularly limited. For example, the method for measurement according to the present invention can be applied to biological samples such as whole blood, plasma, serum, blood cells, urine, and spinal fluid, drinks such as juices, and foods such as soy sauce and Worcestershire sauce. Among these, the method particularly is useful for the blood samples such as whole blood, plasma, serum, and blood cells as described above and the biological samples other than those, for example.

Furthermore, even when the whole blood sample contains, for example, an exogenous glycated amino acid or the like, the measurement still can be carried out with high accuracy. For example, even though the exogenous glycated amino acid is present in whole blood only temporarily, it has a considerable influence on the measured value of a glycated protein or the like when it is contained in whole blood. However, according to the present invention, such an influence can be eliminated.

While the whole blood sample is not particularly limited, the method for measurement according to the present invention is useful for a whole blood sample collected from a patient after being put on an intravenous drip, for example. This is because the variation in the measured value due to an exogenous glycated amino acid being formed is observed especially in a sample collected from a patient after being put on an intravenous drip.

In the method for measurement according to the present invention, the analyte is not particularly limited as long as a redox reaction is utilized. For example, the analyte may be components in whole blood, components in erythrocytes, components in plasma, components in serum, components in urine, components in spinal fluid, and the like, and it is preferably a component in erythrocytes. For example, when a component in erythrocytes is to be measured, whole blood itself may be hemolyzed to prepare a sample, or erythrocytes may be separated from whole blood and hemolyzed to prepare a sample.

In the method for measurement according to the present invention, examples of the glycated amine as the analyte include glycated proteins, glycated peptides, and glycated amino acids. Specifically, the analyte may be a glycated protein such as a glycated hemoglobin or a glycated albumin. When a glycated hemoglobin as a component in erythrocytes is to be measured, whole blood itself may be hemolyzed to prepare a sample, or erythrocytes are separated from whole blood and hemolyzed to prepare a sample, for example.

BRIEF DESCRIPTION OF DRAWINGS

FIG. 1 is a graph showing the correlation between the amount of HbAlc measured by the method for measurement using FAODs according to one example of the present invention and that measured using an automatic analysis apparatus.

BEST MODE FOR CARRYING OUT THE INVENTION

In the method for measurement according to the present invention, FAODs catalyzing a reaction represented by Formula (1) below preferably are used. Examples of such FAODs include a FAOD specific for a glycated amine having a glycated α-amino group (hereinafter referred to as a "FAOD-a"), a FAOD specific for a glycated amine having a glycated amino group in a side chain of an amino acid residue (hereinafter referred to as a "FAOD-S"), and a FAOD specific for both a glycated amine having a glycated α-amino group and a glycated amine having a glycated amino group in a side of an amino acid residue (hereinafter referred to as a "FAOD-αS").

$$R^1—CO—CH_2—NH—R^2+H_2O+O_2 \rightarrow R^1—CO—CHO+NH_2—R^2+H_2O_2 \quad (1)$$

In Formula (1), $R^1$ denotes a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by $$—[CH(OH)]_n—CH_2OH$$

where n is an integer of 0 to 6.

In Formula (1), $R^2$ is not particularly limited. However, when the glycated amine is a glycated amino acid or a glycated peptide, there is a difference between the case where an α-amino group is glycated and the case where an amino group other than the α-amino group (i.e., an amino group in a side chain of an amino acid residue) is glycated.

In Formula (1), when an α-amino group is glycated, $R^2$ is an amino acid residue or a peptide residue represented by Formula (2) below. The above-described FAOD-α and FAOD-αS specifically catalyze the reaction represented by Formula (1) in this case.

$$—CHR^3—CO—R^4 \quad (2)$$

In Formula (2), $R^3$ denotes an amino-acid side chain group. $R^4$ denotes a hydroxyl group, an amino acid residue, or a peptide residue, and can be represented, for example, by Formula (3) below. In Formula (3), n is an integer of 0 or more, and $R^3$ denotes an amino-acid side chain group as in the above. When n is an integer of more than 1, the amino-acid side chain groups may be either the same or different.

$$—(NH—CHR^3—CO)_n—OH \quad (3)$$

In Formula (1), when an amino group other than the α-amino group is glycated (i.e., an amino-acid side chain group is glycated), $R^2$ can be represented by Formula (4) below. The above-described FAOD-S and FAOD-αS specifically catalyze the reaction represented by Formula (1) in this case.

$$—R^5—CH(NH—R^6)—CO—R^7 \quad (4)$$

In Formula (4), $R^5$ denotes a portion other than the glycated amino group in the amino-acid side chain group. For example, when the glycated amino acid is lysine, $R^5$ is as follows.

$$—CH_2—CH_2—CH_2—CH_2—$$

For another example, when the glycated amino acid is arginine, $R^5$ is as follows.

$$—CH_2—CH_2—CH_2—NH—CH(NH_2)—$$

In Formula (4), $R^6$ denotes hydrogen, an amino acid residue, or a peptide residue, and can be represented, for example, by Formula (5) below. In Formula (5), n denotes an integer of 0 or more, and $R^3$ denotes an amino-acid side chain group as in the above. When n is an integer of more than 1, amino-acid side chain groups may be either the same or different.

$$—(CO—CHR^3—NH)_n—H \quad (5)$$

In Formula (4), $R^7$ denotes a hydroxyl group, an amino acid residue, or a peptide residue, and can be represented, for example, by Formula (6) below. In Formula (6), n is an integer of 0 or more, and $R^3$ denotes an amino-acid side chain group as in the above. When n is an integer of more than 1, the amino-acid side chain groups may be either the same or different.

$$—(NH—CHR^3—CO)_n—OH \quad (6)$$

Examples of the FAOD-αspecific for a glycated α-amino group include a commercially available product named Fructosyl-Amino Acid Oxidase (FAOX-E) (manufactured by Kikkoman Corporation) and FAODs derived from the genus Penicillium (JP 8 (1996)-336386 A). Examples of the FAOD-S specific for a glycated side chain of an amino acid residue include FAODs derived from the genus Fusarium ("Conversion of Substrate Specificity of Amino Acid Oxidase Derived from Fusarium oxysporum" by Maki FUJIWARA et al., Annual Meeting 2000, The Society for Biotechnology, Japan). Furthermore, examples of FAOD-αS specific for both a glycated α-amino group and a glycated side chain group of an amino acid residue include a commercially available product named FOD (manufactured by Asahi Chemical Industry Co., Ltd.), FAODs derived from the genus Gibberella (JP 8 (1996)-154672 A), FAODs derived from the genus Fusarium (JP 7 (1995)-289253 A), and FAODs derived from the genus Aspergillus (WO 97/20039).

Hereinafter, the method for measurement according to the present invention will be described in detail with reference to the following examples, in which a glycated protein derived from blood cells is measured using a whole blood sample containing a glycated amino acid as a non-analyte glycation product. In the present invention, unless otherwise stated, "a glycated amino acid as a non-analyte glycation product" refers to the one contained in the sample before starting the measurement and does not include a degradation product of the glycated protein as the analyte obtained by the treatment with a protease.

FIRST EMBODIMENT

The present embodiment is one example of the first method, in which a FAOD-α is used to degrade the glycated amino acid and a FAOD-αS is used to measure the glycated protein.

First, whole blood is hemolyzed to prepare a hemolyzed sample. The method of causing the hemolysis is not particularly limited, and can be, for example, a method using a surfactant, a method using ultrasonic waves, a method utilizing a difference in osmotic pressure, and a method using a freeze-thawing technique. Among these, the method using a surfactant is preferable because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are products named Triton X-100, Tween-20, Brij 35, and the like. The conditions for the treatment with the surfactant usually are as follows: when the concentration of blood cells in the solution to be treated is in the range from 1 to 10 vol %, the surfactant is added so that its concentration in the solution falls in the range from 0.1 to 1 wt %, and stirred at room temperature for about 5 seconds to 1 minute.

Furthermore, when utilizing the difference in osmotic pressure, to the whole blood is added 2 to 100 times its volume of purified water to cause hemolysis, for example.

Next, the hemolyzed sample is treated with a protease. This protease treatment is carried out to degrade the glycated protein so that a FAOD described later can act thereon more easily. The type of the protease is not particularly limited, and for example, the above-described proteinase K, subtilisin, trypsin, aminopeptidase, papain, metalloproteinases, and the like can be used. The protease treatment usually is carried out in a buffer, and the conditions of the treatment are determined as appropriate depending on the type of the protease used, the type and the concentration of the glycated protein as the analyte, etc.

When the sample is treated using trypsin as the protease, the protease treatment is carried out, for example, under the conditions as follows: the concentration of the protease in the reaction solution in the range from 100 to 6000 U/l; the concentration of blood cells in the reaction solution in the range from 0.2 to 5 vol %; the reaction temperature in the range from 20° C. to 50° C.; the reaction period in the range from 10 minutes to 20 hours; and the pH in the range from 6 to 9. The treatment usually is carried out in a buffer. The type of the buffer is not particularly limited, and for example, Tris-HCl buffer, phosphate buffer, EPPS buffer, PIPES buffer, and the like can be used.

Next, the hemolyzed sample treated with the protease is treated with a FAOD-α catalyzing the reaction represented by Formula (1) above, more specifically the reaction represented by Formula (7) below.

$$R^1—CO—CH_2—NH—CHR^3—COOH+H_2O+O_2 \rightarrow R^1—CO—CHO+NH_2—CHR^3—COOH+H_2O_2 \quad (7)$$

In Formula (7), $R^1$ denotes a sugar residue as in the above, and $R^3$ denotes an amino-acid side chain group as in the above.

By this treatment, the glycated amino acid having a glycated α-amino group and the glycated α-amino group of the glycated protein degradation product contained in the hemolyzed sample are degraded.

According to this FAOD-α treatment, among various glycated amino acids, the one having a glycated side-chain amino group remains without being degraded. However, considering the ratio of the glycated amino acid having a glycated side-chain amino group to the glycated amino acids as a whole and the ratio of the same to amino acid residues having a glycated side-chain amino group in glycated proteins, it can be said that the influence of the remaining glycated amino acid is small so that the accuracy of the measurement can be improved sufficiently.

The FAOD-α treatment is carried out, for example, under the conditions as follows: the concentration of the FAOD-α in the reaction solution in the range from 10 to 5000 U/l, the concentration of the blood cells in the reaction solution in the range from 0.5 to 20 vol %, the reaction temperature in the range from 20° C. to 50° C., the reaction period in the range from 1 minute to 1 hour, and the pH in the range from 6 to 9. The FAOD-α treatment usually is carried out in a buffer, and the same buffers as in the protease treatment also can be used in the FAOD-α treatment.

Subsequently, the hemolyzed sample treated with the FAOD-α is treated further with a FAOD-αS. As described above, the FAOD-αS acts on both a glycated α-amino group and a glycated side-chain amino group. However, since the glycated protein degradation product has been treated with the degradation FAOD-α in advance, it is possible to cause this measurement FAOD-αS to act only on the glycated side-chain amino group of the glycated protein degradation product.

Similarly to the above-described protease treatment, this FAOD-αS treatment preferably is carried out in a buffer. The type of the buffer is not particularly limited, and the same buffers as in the protease treatment also can be used in the FAOD-αS treatment.

The FAOD-αS treatment is carried out, for example, under the conditions as follows: the concentration of the FAOD-αS in the reaction solution in the range from 10 to 30,000 U/l, the concentration of the blood cells in the reaction solution in the range from 0.1 to 5 vol %, the reaction temperature in the range from 20° C. to 50° C., the reaction period in the range from 1 minute to 1 hour, and the pH in the range from 6 to 9.

Next, the hydrogen peroxide formed by the FAOD-αS treatment is measured by causing a further redox reaction using a POD and a color-developing substrate.

As the color-developing substrate, N-(carboxymethylaminocarbonyl)-4,4'-bis(dimethylamino)diphenylamine sodium salt, orthophenylenediamine (OPD), a substrate in which a Trinder's reagent and 4-aminoantipyrine are combined, and the like can be used, for example. Examples of the Trinder's reagent include phenols, phenol derivatives, aniline derivatives, naphthols, naphthol derivatives, naphthylamine, and naphthylamine derivatives. Furthermore, in place of the aminoantipyrine, it is possible to use aminoantipyrine derivatives, vanillin diamine sulfonic acid, methylbenzothiazolinone hydrazone (MBTH), sulfonated methylbenzothiazolinone hydrazone (SMBTH), and the like. Among these color-developing substrates, N-(carboxymethylaminocarbonyl)-4,4'-bis (dimethylamino)diphenylamine sodium salt is particularly preferable.

The redox reaction usually is carried out in a buffer. The conditions of the reaction are determined as appropriate depending on the concentration of the hydrogen peroxide formed, etc. The conditions are usually as follows: the concentration of the POD in the reaction solution in the range from 10 to 100,000 IU/l; the concentration of the color-developing substrate in the reaction solution in the range from 0.005 to 30 mmol/l; the reaction temperature in the range from 15° C. to 37° C.; the reaction period in the range from 0.1 to 30 minutes; and the pH in the range from 5 to 9. Moreover, the type of the buffer is not particularly limited, and for example, the same buffers as in the protease treatment and the FAOD treatments can be used.

In the redox reaction, for example, when the color-developing substrate is used, the amount of the hydrogen peroxide can be determined by measuring the degree of the color developed (i.e. absorbance) in the reaction solution with a spectrophotometer. Then, the amount of the glycated protein in the sample can be determined using the concentration of the hydrogen peroxide and a calibration curve or the like, for example. In the present embodiment, the amount of the glycated protein is determined based on the amount of a glycated amino group in a side chain of an amino acid residue.

The hydrogen peroxide formed by the degradation FAOD-α added first reacts with catalase present in the blood sample (hemolyzed sample) and is removed. Thus, it does not have any influence on the measurement of the hydrogen peroxide derived from the analyte formed by the FAOD-αS. The hydrogen peroxide formed by the FAOD-α may be removed by adding catalase. When the hydrogen peroxide is removed by the reaction with catalase, in order to prevent the hydrogen peroxide formed by the FAOD-αS treatment to be performed later from also being removed, it is preferable to add excessive amounts of POD and color-developing substrate when adding the FAOD-αS. In this case, the POD preferably is added so that its activity (U) becomes 5 to 100 times that of the catalase added, for example.

The amount of the hydrogen peroxide can be determined not only by the above-described enzymatic method using the POD etc. but also by an electrical method, for example.

In this measurement, the protease treatment in not necessarily performed before the degradation FAOD-α treatment as described above, and may be performed after the FAOD-α treatment, for example. As described above, the protease treatment is carried out so that the FAODs can act more easily.

However, since the FAOD-α treatment is carried out in order to degrade the glycated amino acid, the effect of the present invention can be obtained sufficiently even if the glycated protein is not degraded with the protease prior to the FAOD-α treatment.

The method for measurement according to the present embodiment also is applicable, for example, when the non-analyte glycation product is a glycated amino acid having a glycated α-amino group and the glycated amine as the analyte is a glycated protein having a glycated α-amino group. In this case, even if a degradation FAOD does not act on the glycated protein easily, there is a possibility that the remaining degradation FAOD may act on the glycated protein degradation product obtained by the protease treatment, for example. On this account, it is preferable to inactivate the remaining FAOD by the degradation treatment with a protease as in a second embodiment described later, or to adjust the ratio of a degradation FAOD to a measurement FAOD added to the sample as in a third embodiment described later.

SECOND EMBODIMENT

The present embodiment is one example of the second method in which the same FAOD is used to degrade a glycated amino acid as a non-analyte glycation product and to measure a glycated protein as an analyte. The FAOD used in not particularly limited, and for example, any of a FAOD-α, a FAOD-S, and a FAOD-αS may be used.

A hemolyzed sample is prepared in the same manner as in the first embodiment, and a degradation FAOD is added to this hemolyzed sample.

The treatment is carried out, for example, under the conditions as follows: the concentration of the FAOD in the reaction solution in the range from 10 to 5000 U/l, the concentration of the blood cells in the reaction solution in the range from 0.5 to 20 vol %, the reaction temperature in the range from 20° C. to 50° C., the reaction period in the range from 1 minute to 1 hour, and the pH in the range from 6 to 9. This treatment usually is carried out in a buffer, and the same buffers as described above also can be used in this treatment.

Next, the sample treated with the FAOD is treated with a protease. A first object of this protease treatment is to degrade the glycated protein derived from blood cells so that a measurement FAOD to be added later can act thereon more easily, as described above. A second object of the protease treatment is to inactivate the degradation FAOD by digesting it.

Since FAODs have properties that they do not act on glycated proteins easily whereas they act on glycated amino acids easily, the glycated amino acid in the sample is degraded first in the treatment with the degradation FAOD. However, if the glycated protein is treated with the protease in the state where the degradation FAOD still remains, there arises a problem in that the remaining FAOD reacts with the glycation site of the glycated protein degradation product so that the glycated protein cannot be measured accurately. This problem can be solved by inactivating the remaining FAOD with the protease to prevent the remaining FAOD from reacting with the glycated protein degradation product. To this end, the amount of the protease to be added needs to be sufficient to allow the degradation FAOD added first to be inactivated rapidly and also the glycated protein to be degraded.

The type of the protease is not particularly limited, and the same proteases as described above also can be used. The conditions of the protease treatment are determined as appropriate depending on the type of the protease used, the type and the concentration of the glycated protein, the type and the amount of the degradation FAOD, etc.

The protease is added so that its concentration in the reaction solution of the protease treatment falls, for example, in the range from 1 to 1,000,000 KU/l, preferably from 10 to 300,000 KU/l, and more preferably from 100 to 100,000 KU/l, when the concentration of the degradation FAOD is 100 U/l.

Specifically, when the sample is treated using trypsin as the protease, the protease treatment is carried out, for example, under the conditions as follows: the concentration of the protease in the reaction solution in the range from 1000 to 30,000 KU/l; the concentration of blood cells in the reaction solution in the range from 0.2 to 5 vol %; the concentration of the FAOD in the reaction solution in the range from 10 to 1000 U/l; the reaction temperature in the range from 20° C. to 50° C.; the reaction period in the range from 10 minutes to 20 hours; and the pH in the range from 6 to 9.

Subsequently, the same FAOD as the degradation FAOD is added again as a measurement FAOD to treat the glycated protein degradation product obtained by the protease treatment. It is necessary to add a sufficient amount of the measurement FAOD because there is a possibility that the measurement FAOD may be inactivated with the protease.

The measurement FAOD treatment also preferably is carried out in a buffer as in the above. The type of the buffer is not particularly limited, and the same buffers as in the protease treatment also can be used in this measurement FAOD treatment.

The measurement FAOD is added so that its concentration in the reaction solution of this measurement FAOD treatment is, for example, in the range from 10 to 1,000,000 U/l, preferably 100 to 200,000 U/l, and more preferably 500 to 50,000 U/l when the concentration of the protease is 10,000 KU/l.

Specifically, the conditions of the measurement FAOD treatment are, for example, as follows: the concentration of the FAOD in the reaction solution in the range from 500 to 20,000 U/l; the concentration of the protease in the reaction solution in the range from 100 to 30,000 KU/l; the concentration of blood cells in the reaction solution in the range from 0.01 to 1 vol %; the reaction temperature in the range from 15° C. to 40° C.; the reaction period in the range from 1 minute to 1 hour; and the pH in the range from 6 to 9.

According to the present embodiment, even if the same FAOD is used to degrade the glycated amino acid and to measure the glycated protein, the glycated protein can be measured with high accuracy without being affected by the glycated amino acid.

THIRD EMBODIMENT

The present embodiment is an example where the same FAOD is used to degrade a glycated amino acid as a non-analyte glycation product and to measure a glycated protein as an analyte. However, the present embodiment differs from the above-described second embodiment in that it is not always necessary to inactivate a degradation FAOD with a protease. Because of the substrate specificity of enzymes, inactivating a FAOD with a protease can be difficult depending on the combination of the FAOD and protease. A method for measurement according to the present embodiment is effective in such a case. If a degradation FAOD added first reacts with a glycated protein degradation product formed by the treatment with a protease, the accuracy of the measurement cannot be improved. Accordingly, it is important to adjust the ratio of a degradation FAOD to a measurement FAOD added to a sample as described later.

First, a hemolyzed sample is prepared in the same manner as in the first embodiment, and a degradation FAOD is added to this hemolyzed sample.

When it is difficult to inactivate the degradation FAOD with the protease used, the degradation FAOD needs to be added in an amount such that, even if the activity of the degradation FAOD remains during the protease treatment, it does not act on the glycated protein degradation product formed. FAODs have properties that they do not act on glycated proteins easily and act on glycated amino acids still more easily than on glycated peptides. Therefore, the amount of the degradation FAOD to be added and the reaction period preferably are set so as to allow the degradation FAOD to act only on the glycated amino acid, for example.

The conditions of the FAOD treatment are, for example, as follows: the concentration of the FAOD in the reaction solution in the range from 10 to 5000 U/l; the concentration of blood cells in the reaction solution in the range from 0.2 to 20 vol %; the reaction temperature in the range from 20° C. to 50° C.; the reaction period in the range from 1 minute to 1 hour; and the pH in the range from 6 to 9. This treatment usually is carried out in a buffer, and the same buffers as described above also can be used in this treatment.

Next, the sample treated with the FAOD is treated with a protease. Since the present embodiment is an example where the protease hardly acts on the FAOD, the amount of the protease to be added is not particularly limited.

The type of the protease is not particularly limited, and the same proteases as described above also can be used. The conditions of the protease treatment are determined as appropriate depending on the type of the protease used, the type and the concentration of the glycated protein as the analyte, the type and the concentration of the FAOD added first, and the substrate specificity of the protease used with respect to the FAOD, etc., as described above.

Examples of the combination of a FAOD and a protease falling within the present embodiment include the combination of a product named FOD (Asahi Chemical Industry Co., Ltd.) and a product named Toyoteam (Toyobo Co., Ltd.) and the combination of a FAOD derived from the genus Gibberella and a product named Proteinase K (Roche).

When the sample is treated using trypsin as the protease, the protease treatment is carried out, for example, under the conditions as follows: the concentration of the protease in the reaction solution in the range from 100 to 6000 U/l; the concentration of blood cells in the reaction solution in the range from 0.2 to 5 vol %; the concentration of the FAOD in the reaction solution in the range from 0.1 to 100 U/l; the reaction temperature in the range from 20° C. to 50° C.; the reaction period in the range from 10 minutes to 20 hours; and the pH in the range from 6 to 9.

Subsequently, the same FAOD as the degradation FAOD is added again as a measurement FAOD so that it acts on the glycated protein degradation product obtained by the protease treatment.

The measurement FAOD treatment also preferably is carried out in a buffer as in the above. The type of the buffer is not particularly limited, and the same buffers as in the protease treatment also can be used in this measurement FAOD treatment.

Thus, in the present embodiment, the ratio (activity ratio A:B) of the degradation FAOD (A) to the measurement FAOD (B) added to the sample is set, for example, in the range from 1:50,000 to 1:10, preferably 1:5000 to 1:25, and more preferably 1:500 to 1:50, as described above. Unlike the above-described second embodiment, the degradation FAOD remains in the reaction solution in the present embodiment. However, when the ratio is in the above-described range, the remaining degradation FAOD does not act on the glycated protein degradation product during the protease treatment to such an extent that it affects the measurement because the reaction velocity of the remaining degradation FAOD is very low.

The conditions of the measurement FAOD treatment are, for example, as follows: the concentration of the FAOD in the reaction solution in the range from 500 to 20,000 U/l; the concentration of the protease in the reaction solution in the range from 100 to 30,000 KU/l; the concentration of blood cells in the reaction solution in the range from 0.01 to 1 vol %; the reaction temperature in the range from 15° C. to 40° C.; the reaction period in the range from 1 minute to 1 hour; and the pH in the range from 6 to 9.

EXAMPLES

Example 1 and Comparative Example 1

A fluid containing an amino acid and D-glucose was administered to a patient via an intravenous drip, and the blood of the patient was collected 1 hour later. The blood was centrifuged (1000 g, 10 min) to separate blood cells and plasma. Then, 0.45 ml of the following hemolysis reagent A was mixed with 0.006 ml of the blood cell fraction and 0.006 ml of the plasma fraction to hemolyze the blood cells. In this manner, a plurality of hemolyzed samples were prepared.

(Hemolysis Reagent A: pH 8.5)

| | |
|---|---|
| Product named TAPS (Dojindo Laboratories) | 140 mmol/l |
| Glycinamide (Nacalai Tesque, Inc.) | 60 mmol/l |
| Polyoxyethylene lauryl ether (Nacalai Tesque, Inc.) | 24 g/l |

Then, 0.0023 ml of solutions containing the following various FAODs (concentration: 200 KU/l) respectively were added to the hemolyzed samples at 25° C., and the resultant mixtures were incubated at 37° C. for 40 minutes. In the following paragraph, the (1) FAOD derived from the genus Penicillium is specific for a glycated α-amino group, the (2) FAOD derived from the genus Aspergillus is specific for a glycated α-amino group and a glycated ϵ-amino group, and the (3) FAOX-E is specific for a glycated α-amino group.

(Used FAOD)

(1) FAOD derived from the genus Penicillium (JP 8 (1996)-336386 A)

(2) FAOD derived from the genus Aspergillus (WO 99/20039)

(3) Product named FAOX-E (Kikkoman Corporation, hereinafter the same)

Next, to 0.01 ml of the hemolyzed samples respectively containing the above-described FAODs were added 0.01 ml of purified water and further 0.065 ml of the following protease reagent, and the resultant mixtures were incubated at 37° C. for 5 minutes. Subsequently, 0.045 ml of the following color-developing reagent further was added, and the resultant mixtures were incubated at 37° C. for 3 minutes. Then, the absorbance (at the wavelength of 751 nm) was measured with a measuring apparatus (product name JCA-BM 8, manufactured by Japan Electron Optics Laboratory Co. Ltd.). On the other hand, as Comparative Example 1, the measurement was carried out in the same manner as in Example 1 except that purified water was added to a hemolyzed sample instead of the various FAODs. Furthermore, as a control test, the measurement was carried out in the same manner as in Example 1 except that purified water was mixed with blood cells instead of the plasma. The results are shown in Table 1 below.

(Protease Reagent: pH 6.5)

| | |
|---|---|
| MOPS (Dojindo Laboratories) | 5 mmol/l |
| Tetrazolium compound (product name WST-3, Dojindo Laboratories) | 2 mmol/l |
| $NaN_3$ (Nacalai Tesque, Inc.) | 0.05 g/l |
| $CaCl_2$ (Nacalai Tesque, Inc.) | 5 mmol/l |
| NaCl (Nacalai Tesque, Inc.) | 300 mmol/l |
| Metalloproteinase | 3 g/l |

(Color-Developing Reagent)

| | |
|---|---|
| FAOD derived from the genus *Gibberella* (JP 8(1996)-154672 A) | 26.0 KU/l |
| POD (Toyobo Co., Ltd) | 77.6 KU/l |
| Color-developing substrate (product name DA-64, Wako Pure Chemical Industries, Ltd.) | 0.052 mmol/l |
| Tris-HCl buffer (pH 6.9) | 200 mmol/l |

TABLE 1

| | Type of FAOD | Absorbance after 40 minutes (Abs.) |
|---|---|---|
| Control test | FAOD: added/Plasma: not added | 0.008 |
| Ex. 1 | (1) FAOD derived from the genus *Penicilium* | 0.009 |
| | (2) FAOD derived from the genus *Aspergillus* | 0.009 |
| | (3) Product named FAOX-E | 0.008 |
| Com. Ex. 1 | FAOD: not added | 0.020 |

As shown in Table 1, since the glycated amino acid contained in the plasma also reacted with the FAOD contained in the color-developing reagent in Comparative Example 1, the higher absorbance was exhibited in Comparative Example 1 than in the control test by which only the glycated protein contained in the blood cells was measured. In contrast, the glycated protein could be measured accurately in Example 1 because the glycated amino acid contained in the plasma was treated with the FAOD in advance, and hence, Example 1 exhibited a high correlation with the control test. This is because the FAOD contained in the color-developing reagent could act only on the degradation product of the glycated protein derived from the blood cells in Example 1.

Example 2 and Comparative Example 2

The blood of the patient after who had been put on an intravenous drip was collected in the same manner as in Example 1 and was left to stand still. Then, the blood cells having precipitated naturally were collected, and 0.01 ml of this blood cell fraction was mixed with 0.3 ml of the following hemolysis reagent B to prepare a hemolyzed sample. The Hb concentration and HbAlc concentration of this hemolyzed sample were analyzed with the above-described measuring apparatus (automatic analysis apparatus). Since the blood cells having precipitated naturally were collected, the blood cell fraction contained components in plasma.

(Hemolysis Reagent B: pH 8.5)

| | |
|---|---|
| Product named TAPS (Dojindo Laboratories) | 140 mmol/l |
| Glycinamide (Nacalai Tesque, Inc.) | 60 mmol/l |
| Polyoxyethylene lauryl ether (Nacalai Tesque, Inc.) | 24 g/l |
| Product named FAOX-E (Kikkoman Corporation, hereinafter the same) | 1 KU/l |

To 0.01 ml of the hemolyzed sample were added 0.01 ml of purified water and 0.065 ml of the above-described protease reagent, and the resultant mixture was incubated at 37° C. The absorbance at the wavelength of 571 nm was measured after 4.5 minutes from the start of the incubation. The absorbance thus measured was regarded as the absorbance showing the Hb concentration. Then, after 5 minutes from the start of the incubation, 0.045 ml of the same color-developing reagent as used in Example 1 was added, and the resultant mixture was incubated at 37° C. for 3 minutes. The mixture was allowed to react further. Then, after 3 minutes from the start of the reaction, the absorbance at the wavelength of 751 nm was measured using the above-described automatic analysis apparatus. The absorbance thus measured was regarded as the absorbance showing the HbAlc concentration.

Thereafter, the thus-measured absorbances were substituted into previously prepared calibration curves showing the relationships between a Hb concentration (g/l) and absorbance and between a HbAlc concentration (g/l) and absorbance, respectively, to determine the Hb concentration and the HbAlc concentration. Then, HbAlc % was calculated using the following equation.

$$\text{HbAlc (\%)} = (\text{HbAlc concentration}/\text{Hb concentration}) \times 100$$

The calibration curves were prepared in the following manner. First, standard solutions with various known concentrations of HbAlc and Hb were provided. Then, the HbAlc concentration and the Hb concentration of these standard solutions were measured using an automatic measuring apparatus (product name HA-8150, manufactured by ARKRAY, INC.). On the other hand, with respect to these standard solutions, the absorbance corresponding to the HbAlc concentration and the absorbance corresponding to the Hb concentration were measured in the same manner as described above. Based on the measured values given by the automatic measuring apparatus and the absorbances thus measured, primary regression equations were prepared, which were used as the calibration curves.

On the other hand, as Comparative Example 2, the measurement was carried out in the same manner as in Example 2 except that the hemolysis reagent A not containing the product named FAOX-E was added to the blood cells instead of the hemolysis reagent B.

Furthermore, as a control test, the measurement was carried in the following manner. To 0.05 ml of the blood cell fraction collected after letting blood cells precipitate naturally was added 2.5 ml of a diluent dedicated for the automatic measuring apparatus HA-8150 to cause hemolysis, thus preparing a hemolyzed sample. The HbAlc concentration (%) of this hemolyzed sample was measured with the automatic measuring apparatus (the product name HA-8150: available from ARKRAY, INC.).

The results of the above-described measurements are shown in FIG. 1. FIG. 1 is a graph showing the relationship between the HbAlc (%) in Example 2 and Comparative Example 2 measured by the enzymatic method and the HbAlc (%) obtained by the automatic analysis as the control test. In FIG. 1, Example 2 has a correlation equation of "y=1.079x−0.409" and a correlation coefficient of "0.967" while Comparative Example 2 has a correlation equation of "y=1.124x−0.559" and a correlation coefficient of "0.931".

In Example 2, the exogenous glycated amino acid contained in the plasma was degraded by the FAOD (contained in the hemolysis reagent B) treatment carried out first, and the hydrogen peroxide formed by this treatment was removed by the reaction with catalase present in the sample. Therefore, in the redox reaction caused by the FAOD added later, only hydrogen peroxide derived from the glycated protein in the blood cells was formed. Thus, as shown in FIG. 1, the value obtained in Example 2 was very close to the value obtained by the automatic analysis with respect to the sample containing no plasma as the control test. Furthermore, Example 2 exhibited the extremely high correlation coefficient (0.967) with the control test. On the other hand, in Comparative Example 2, the FAOD caused to act on the glycated protein also reacted with the glycated amino acid contained in the plasma. As a result, more hydrogen peroxide was formed than was derived from the glycated protein. Accordingly, HbAlc (%) obtained in Comparative Example 2 was greater than the HbAlc (%) obtained by the control test, and Comparative Example 2 exhibited a lower correlation coefficient (0.931) with the control test than Example 2.

INDUSTRIAL APPLICABILITY

As specifically described above, according to the method of pretreating a sample of the present invention, a glycated peptide or a glycated amino acid as a non-analyte glycation product contained in the sample can be degraded so as to be removed. Therefore, by carrying out measurement of a glycated amine with respect to the sample pretreated by this method, the influence of the non-analyte glycation product can be eliminated, which allows excellent accuracy of the measurement to be achieved. Thus, when the sample is blood collected from a patient after being put on an intravenous drip and thus contains an exogenous glycated amino acid and the like that are present only temporarily, the influence of these substances can be eliminated. Accordingly, by applying the method to, for example, the measurement of a glycated hemoglobin contained in erythrocytes, the measurement can be carried out with higher accuracy than in conventional methods, which further increases the importance of the glycated hemoglobin as an index in the diagnosis and the like of diabetes.

The invention claimed is:

1. A method of pretreating a sample containing a glycated amine as an analyte, comprising:

pretreating said sample by adding a first fructosyl amino acid oxidase to said sample to act on a glycated amino acid or a glycated peptide present in the sample other than the analyte so as to remove the glycated amino acid or the glycated peptide by degrading it;

adding a second fructosyl amino acid oxidase to said sample after the pretreatment to react with the analyte or the degradation product of the analyte to form hydrogen peroxide; and measuring the amount of hydrogen peroxide by a redox reaction to determine the amount of the analyte.

2. The method according to claim 1, wherein the first fructosyl amino acid oxidase used in the pretreating step has a substrate specificity different from that of the second fructosyl amino acid oxidase that reacts with the analyte or the degradation product of the analyte.

3. The method according to claim 2, wherein the first fructosyl amino acid oxidase used in the pretreating step is specific for a glycated α-amino group, and the second fructosyl amino acid oxidase that reacts with the analyte or the degradation product of the analyte is specific for a glycated α-amino group and a glycated side chain of an amino acid residue.

4. The method according to claim 3, wherein the glycated amino acid present in the sample other than the analyte is a glycated amino acid having a glycated α-amino group, and the analyte is a glycated protein or a glycated peptide having a glycated α-amino group and a glycated side chain of an amino acid residue.

5. The method according to claim 2, further comprising:

degrading the analyte with a protease to give a degradation product of the analyte either before or after the pretreating step.

6. The method according to claim 5, wherein the protease is at least one protease selected from the group consisting of metalloproteinases, bromelain, papain, trypsin, proteinase K, subtilisin, and aminopeptidase.

7. The method according to claim 6, wherein the protease is at least one protease that degrades a glycated hemoglobin selectively and is selected from the group consisting of metalloproteinases, bromelain, papain, trypsin derived from porcine pancreas, and protease derived from Bacillus subtilis.

8. The method according to claim 1, further comprising:

degrading the analyte with a protease to give a degradation product of the analyte after the pretreating step, wherein the second fructosyl amino acid oxidase that reacts with the analyte or the degradation product of the analyte is same as the first fructosyl amino acid used in the pretreating step.

9. The method according to claim 8, wherein the first fructosyl amino acid oxidase used in the pretreating step is inactivated with the protease.

10. The method according to claim 8, wherein the first fructosyl amino acid oxidase (A) used in the pretreating step and the second fructosyl amino acid oxidase (B) that reacts with the analyte or the degradation product of the analyte are added respectively to the sample so that a ratio (activity ratio A:B) of the first fructosyl amino acid oxidase (A) to the second fructosyl amino acid oxidase (B) is in a range from 1:10 to 1:50,000.

11. The method according to claim 8, wherein a glycation site of the glycated amino acid or a glycated peptide is an α-amino group, the analyte is a glycated protein, and a glycation site of the protein is an α-amino group.

12. The method according to claim 8, wherein the protease is at least one protease selected from the group consisting of metalloproteinases, bromelain, papain, trypsin, proteinase K, subtilisin, and aminopeptidase.

13. The method according to claim 12, wherein the protease is at least one protease that degrades a glycated hemoglobin selectively and is selected from the group consisting of metalloproteinases bromelain, papain, trypsin derived from porcine pancreas, and protease derived from Bacillus subtilis.

14. The method according to claim 1, wherein the glycated amine is at least one substance selected from the group consisting of glycated amino acids, glycated peptides, and glycated proteins.

15. The method according to claim 14, wherein the glycated proteins are glycated hemoglobins.

16. The method according to claim 1, wherein the sample is at least one biological sample selected from the group consisting of whole blood, plasma, serum, blood cells, urine, and spinal fluid.

17. The method according to claim 16, wherein the sample is a whole blood sample collected from a patient after being put on an intravenous drip.

18. The method according to claim 1, wherein the glycated amino acid present in the sample other than the glycated amine as the analyte includes an exogenous glycated amino acid.

*19. A method of measuring an amount of glycated protein in a sample, comprising:*

*adding fructosyl amino acid oxidase to said sample so as to remove any glycated amino acid or glycated peptide present in said sample other than the glycated protein;*

*subsequently degrading the glycated protein by adding a protease to said sample to form a degradation product of the glycated protein; and*

*measuring the amount of hydrogen peroxide produced by a redox reaction between the fructosyl amino acid oxidase and the degradation product of the glycated protein to determine the amount of the glycated protein.*

*20. The method according to claim 19, wherein the glycated amino acid present in the sample other than the glycated protein is a glycated amino acid having a glycated α-amino group, and wherein the glycated protein has a glycated α-amino group and a glycated side chain of an amino acid residue.*

*21. The method according to claim 20, wherein the protease is at least one protease selected from the group consisting of metalloproteinases, bromelain, papain, trypsin, proteinase K, subtilisin, and aminopeptidase.*

*22. The method according to claim 21, wherein the protease is at least one protease that degrades a glycated hemoglobin selectively and is selected from the group consisting of metalloproteinases, bromelain, papain, trypsin derived from porcine pancreas, and protease derived from Bacillus subtilis.*

*23. The method according to claim 19, wherein the glycated protein is glycated hemoglobin.*

*24. The method according to claim 19, wherein the sample is at least one biological sample selected from the group consisting of whole blood, plasma, serum and blood cells.*

*25. The method according to claim 24, wherein the sample is a whole blood sample collected from a patient after being put on an intravenous drip.*

*26. The method according to claim 19, wherein the glycated amino acid present in the sample other than the glycated protein includes an exogenous glycated amino acid.*

*27. A method of measuring an amount of glycated protein in a sample, comprising:*

*removing a glycated amino acid or a glycated peptide present in said sample other than the glycated protein by adding fructosyl amino acid oxidase to said sample; followed by*

*adding a protease to said sample to degrade the glycated protein, which degraded glycated protein then reacts with the fructosyl amino acid oxidase to form hydrogen peroxide; and*

*measuring the amount of the hydrogen peroxide to determine the amount of the glycated protein.*

*28. The method according to claim 27, wherein the glycated amino acid present in the sample other than the glycated protein is a glycated amino acid having a glycated α-amino group, and wherein the glycated protein has a glycated α-amino group and a glycated side chain of an amino acid residue.*

*29. The method according to claim 28, wherein the protease is at least one protease selected from the group consisting of metalloproteinases, bromelain, papain, trypsin, proteinase K, subtilisin, and aminopeptidase.*

*30. The method according to claim 29, wherein the protease is at least one protease that degrades a glycated hemoglobin selectively and is selected from the group consisting of metalloproteinases, bromelain, papain, trypsin derived from porcine pancreas, and protease derived from Bacillus subtilis.*

*31. The method according to claim 27, wherein the glycated protein is glycated hemoglobin.*

*32. The method according to claim 27, wherein the sample is at least one biological sample selected from the group consisting of whole blood, plasma, serum and blood cells.*

*33. The method according to claim 32, wherein the sample is a whole blood sample collected from a patient after being put on an intravenous drip.*

*34. The method according to claim 27, wherein the glycated amino acid present in the sample other than the glycated protein includes an exogenous glycated amino acid.*

*35. A method of pretreating a sample containing a glycated protein as an analyte, comprising:*

*adding fructosyl amino acid oxidase to said sample to act on a glycated amino acid or a glycated peptide present in the sample other than the analyte so as to remove the glycated amino acid or the glycated peptide by degrading it prior to adding a protease to said sample,*

*wherein the fructosyl amino acid oxidase is at least one of a fructosyl amino acid oxidase specific for a glycated α-amino group (FAOD-α) and a fructosyl amino acid oxidase specific for both a glycated α-amino group and a glycated amino group in a side chain of an amino acid residue (FAOD-αS),*

*wherein the glycated protein is a glycated hemoglobin or a glycated albumin, and*

*wherein the sample is at least one of a plasma sample, a serum sample, or a hemolyzed sample which is prepared by hemolysis of whole blood itself or erythrocytes separated from whole blood.*

*36. The method according to claim 35, wherein the sample is a plasma sample.*

*37. The method according to claim 35, wherein the sample is a serum sample.*

*38. The method according to claim 35, wherein the fructosyl amino acid oxidase is a fructosyl amino acid oxidase specific for a glycated α-amino group (FAOD-α).*

*39. The method according to claim 35, wherein the fructosyl amino acid oxidase is a fructosyl amino acid oxidase specific for both a glycated α-amino group and a glycated amino group in a side chain of an amino acid residue (FAOD-αS).*

* * * * *

UNITED STATES PATENT AND TRADEMARK OFFICE

CERTIFICATE OF CORRECTION

PATENT NO. : RE43,795 E
APPLICATION NO. : 12/903760
DATED : November 6, 2012
INVENTOR(S) : Satoshi Yonehara et al.

It is certified that error appears in the above-identified patent and that said Letters Patent is hereby corrected as shown below:

IN THE SPECIFICATION

Column 1, Line 11, before "TECHNICAL FIELD", insert the following paragraph:

-- More than one reissue application has been filed for the reissue of Patent No. 7,449,305. The reissue applications are Application Nos. 14/751,351; 14/326,697; 13/653,024; and 12/903,760. This application is an application for reissue of U.S. patent application Ser. No. 10/492,140, filed on Apr. 6, 2004, now U.S. Pat. No. 7,449,305, which is a 371 of PCT/JP02/10463, filed on Oct. 9, 2002, which claims foreign priority to Japanese Patent Application No. JP 2001-314218, filed on October 11, 2001. --

Signed and Sealed this
Seventeenth Day of May, 2016

Michelle K. Lee

Michelle K. Lee
*Director of the United States Patent and Trademark Office*